US012729175B2

(12) United States Patent
Karube et al.

(10) Patent No.: US 12,729,175 B2
(45) Date of Patent: Sep. 8, 2026

(54) METHOD FOR PRODUCING COMPOSITION CONTAINING PURIFIED FLUORINE-CONTAINING ETHER COMPOUND

(71) Applicant: DAIKIN INDUSTRIES, LTD., Osaka (JP)

(72) Inventors: Daisuke Karube, Osaka (JP); Kenta Nishimura, Osaka (JP); Yuuki Suzuki, Osaka (JP); Tsubasa Nakaue, Osaka (JP); Yoshichika Kuroki, Osaka (JP); Michiaki Okada, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 593 days.

(21) Appl. No.: 18/135,938

(22) Filed: Apr. 18, 2023

(65) Prior Publication Data

US 2023/0257333 A1 Aug. 17, 2023

Related U.S. Application Data

(63) Continuation of application No. PCT/JP2021/038794, filed on Oct. 20, 2021.

(30) Foreign Application Priority Data

Oct. 21, 2020 (JP) ................................ 2020-176955

(51) Int. Cl.
*C07C 41/22* (2006.01)
*C07C 41/42* (2006.01)

(52) U.S. Cl.
CPC .............. *C07C 41/22* (2013.01); *C07C 41/42* (2013.01)

(58) Field of Classification Search
USPC .......................................................... 568/682
See application file for complete search history.

(56) References Cited

U.S. PATENT DOCUMENTS

2008/0086019 A1 4/2008 Okamoto et al.

FOREIGN PATENT DOCUMENTS

| | | |
|---|---|---|
| CN | 106748676 | 5/2017 |
| JP | 2008-230979 | 10/2008 |
| JP | 2010-501579 | 1/2010 |
| KR | 10-2009-0131049 | 12/2009 |
| KR | 10-2010-0138245 | 12/2010 |
| WO | 2006/123563 | 11/2006 |
| WO | 2008/024508 | 2/2008 |

OTHER PUBLICATIONS

Extended European Search Report issued Sep. 4, 2024 in European Patent Application No. 21882868.9.
International Preliminary Report on Patentability issued Apr. 13, 2023 in International (PCT) Application No. PCT/JP2021/038794.
International Search Report issued Dec. 28, 2021 in International (PCT) Application No. PCT/JP2021/038794.
Ilyin et al., "The Use of Tetrafluorethylene and Hexafluorpropylene in the Synthesis of Partly Fluorinated Alcohols and Dialkyl Ethers", Journal "Fluorine Notes", 2003, No. 5, vol. 30, 21 pages.
Murata et al., "Selective synthesis of fluorinated ethers by addition reaction of alcohols to fluorinated olefins in water", Green Chemistry, 2002, vol. 4, pp. 60-63.

*Primary Examiner* — Ana Z Muresan
(74) *Attorney, Agent, or Firm* — Wenderoth, Lind & Ponack, L.L.P.

(57) ABSTRACT

The present disclosure provides a method for producing a composition comprising a purified fluorine-containing ether compound represented by formula (1): $CHX^1X^2CF_2OX^3$, wherein $X^1$ and $X^2$ are the same or different and each represents a hydrogen atom, a fluorine atom, or a trifluoromethyl group, and $X^3$ represents a $C_{1-6}$ alkyl group, provided that not both $X^1$ and $X^2$ are trifluoromethyl groups.

4 Claims, No Drawings

METHOD FOR PRODUCING COMPOSITION CONTAINING PURIFIED FLUORINE-CONTAINING ETHER COMPOUND

TECHNICAL FIELD

The present disclosure relates to a method for producing a composition comprising a purified fluorine-containing ether compound.

BACKGROUND ART

In recent years, hydrofluoroethers (HFEs), which have a low global warming potential (GWP) and ozone depletion potential (ODP), and low toxicity, are attracting attention as alternatives to chlorofluorocarbons (CFCs) and hydrochlorofluorocarbons (HCFCs).

NPL 1 discloses that 1,1,2,3,3,3-hexafluoropropyl methyl ether (HFE-356mec), a kind of HFE, can be obtained by reacting hexafluoropropene (HFP) with methanol in the presence of alkali.

CITATION LIST

Non-Patent Literature

NPL 1: Green Chemistry, 2002, 4, 60-63

SUMMARY

The present disclosure includes the subject matter described in the following.

A method for producing a composition comprising a purified fluorine-containing ether compound, the method comprising:

(A) reacting, in the presence of a fluorine-containing ether compound represented by formula (1): $CHX^1X^2CF_2OX^3$, wherein $X^1$ and $X^2$ are the same or different and each represents a hydrogen atom, a fluorine atom, or a trifluoromethyl group, and $X^3$ represents a $C_{1-6}$ alkyl group, provided that not both $X^1$ and $X^2$ are trifluoromethyl groups, a fluorine-containing olefin compound represented by formula (2): $CX^1X^2{=}CF(CF_2)_nOX^3$, wherein n represents 0 or 1, and $X^1$, $X^2$, and $X^3$ are as defined above, provided that when $X^1$ or $X^2$ is a trifluoromethyl group, n is 0, and not both $X^1$ and $X^2$ are trifluoromethyl groups, with a halogenating agent and/or oxidant to convert the fluorine-containing olefin compound represented by the formula (2) to a halogen adduct and/or oxide, thereby obtaining a composition comprising the fluorine-containing ether compound represented by the formula (1) and the halogen adduct and/or oxide; and (B) separating the halogen adduct and/or oxide from the composition obtained in the step (A) to obtain a composition comprising a purified fluorine-containing ether compound.

Advantageous Effects

According to the production method of the present disclosure, a composition comprising a purified fluorine-containing ether compound represented by the formula (1) can be produced in a simple manner.

DESCRIPTION OF EMBODIMENTS

As a result of extensive research, the present inventors found that the above object can be achieved by taking advantage of the reaction of the fluorine-containing olefin compound represented by the formula (2) with a halogenating agent and/or oxidant.

The present disclosure has been completed upon further research based on the above finding. Embodiments included in the present disclosure are described in detail below.

In the present specification, the terms "comprise" and "contain" include the concepts of "comprise," "contain," "essentially consist of," and "consist of."

In the present specification, the term "purity" means the component ratio (mass %) determined by quantitative analysis by gas chromatography (GC).

In the present specification, the term "reflux ratio" means the molar flow ratio of reflux liquid and distillate (reflux liquid/distillate).

The pressure described in the present specification is gauge pressure unless otherwise specified. That is, it is expressed as atmospheric pressure=0.0 MPa.

In the present specification, "A and/or B" means either A or B, or both A and B.

In the present specification, "$C_{1-6}$ alkyl groups" refer to methyl, ethyl, propyl, isopropyl, butyl, sec-butyl, tert-butyl, pentyl, and hexyl groups.

1. Method for Producing Composition Comprising Purified Fluorine-Containing Ether Compound The method for producing a composition comprising a purified fluorine-containing ether compound according to the present disclosure (hereinafter also simply referred to as "the production method of the present disclosure") comprises the following steps (A) and (B) in this order. The production method of the present disclosure is described below in the order of steps (A) and (B).

Step (A)

Step (A) is a step of reacting, in the presence of a fluorine-containing ether compound represented by formula (1): $CHX^1X^2CF_2OX^3$, wherein $X^1$ and $X^2$ are the same or different and each represents a hydrogen atom, a fluorine atom, or a trifluoromethyl group, and $X^3$ represents a $C_{1-6}$ alkyl group, provided that not both $X^1$ and $X^2$ are trifluoromethyl groups, a fluorine-containing olefin compound represented by formula (2): $CX^1X^2{=}CF(CF_2)_nOX^3$, wherein n represents 0 or 1, $X^1$ and $X^2$ are the same or different and each represents a hydrogen atom, a fluorine atom, or a trifluoromethyl group, and $X^3$ represents a $C_{1-6}$ alkyl group, provided that when $X^1$ or $X^2$ is a trifluoromethyl group, n is 0, and not both $X^1$ and $X^2$ are trifluoromethyl groups, with a halogenating agent and/or oxidant to convert the fluorine-containing olefin compound represented by the formula (2) to a halogen adduct and/or oxide, thereby obtaining a composition comprising the fluorine-containing ether compound represented by the formula (1) and the halogen adduct of the fluorine-containing olefin compound represented by the formula (2) and/or the oxide of the fluorine-containing olefin compound represented by the formula (2).

In the present disclosure, the fluorine-containing ether compound is represented by the formula (1): $CHX^1X^2CF_2OX^3$, wherein $X^1$, $X^2$, and $X^3$ are as defined above. Specific examples include $CF_3CHFCF_2OX^3$, $CHF_2CF_2OX^3$, $CH_2FCF_2OX^3$, $CH_3CF_2OX^3$, and the like (in all of which, $X^3$ represents a $C_{1-6}$ alkyl group).

The fluorine-containing ether compound represented by the formula (1) is preferably at least one compound selected from the group consisting of $CF_3CHFCF_2OCH_3$, $CHF_2CF_2OCH_3$, $CH_2FCF_2OCH_3$, and $CH_3CF_2OCH_3$. More preferred among these is $CF_3CHFCF_2OCH_3$ (1,1,2,3,3,3-hexafluoropropyl methyl ether: HFE-356mec).

In the present disclosure, the fluorine-containing olefin compound is represented by the formula (2): $CX^1X^2{=}CF(CF_2)_nOX^3$, wherein $X^1$, $X^2$, $X^3$, and n are as defined above. Specific examples include $CF_3CF{=}CFOX^3$, $CF_2{=}CFCF_2OX^3$, $CF_2{=}CFOX^3$, $CHF{=}CFOX^3$, $CH_2{=}CFOX^3$, and the like (in all of which, $X^3$ represents a $C_{1-6}$ alkyl group).

The fluorine-containing olefin compound represented by the formula (2) is preferably at least one compound selected from the group consisting of $CF_3CF{=}CFOCH_3$, $CF_2{=}CFCF_2OCH_3$, $CF_2{=}CFOCH_3$, $CHF{=}CFOCH_3$, and $CH_2{=}CFOCH_3$. More preferred among these is at least one of $CF_3CF{=}CFOCH_3$ and $CF_2{=}CFCF_2OCH_3$.

The halogenating agent is preferably a chlorinating agent and/or brominating agent.

Examples of chlorinating agents include chlorine gas, hypochlorites such as sodium hypochlorite, chlorites such as sodium chlorite, chlorates such as sodium chlorate, interhalogen compounds containing chlorine, and the like. Examples of interhalogen compounds containing chlorine include chlorine monofluoride and the like. Preferred among these chlorinating agents is chlorine gas or sodium hypochlorite. The chlorinating agents can be used singly or in combination of two or more.

Examples of brominating agents include bromine, bromates such as potassium bromate, interhalogen compounds containing bromine, and the like. Examples of interhalogen compounds containing bromine include bromine monofluoride and the like. Preferred among these brominating agents is bromine. The brominating agents can be used singly or in combination of two or more.

Examples of oxidants include hydrogen peroxide water, oxygen, hypochlorites such as sodium hypochlorite, chlorites such as sodium chlorite, chlorates such as sodium chlorite, bromates such as sodium bromide and potassium bromide, and the like. The oxidants can be used singly or in combination of two or more.

Chlorine gas, hypochlorites such as sodium hypochlorite, chlorites such as sodium chlorite, and chlorates such as sodium chlorate can be used as chlorinating agents and oxidants. Further, bromine, and bromates such as potassium bromate, can be used as brominating agents and oxidants.

In the step (A), the halogenating agent and/or oxidant are preferably at least one member selected from the group consisting of chlorine gas, bromine, and sodium hypochlorite.

In the step (A), when the fluorine-containing olefin compound represented by the formula (2) is reacted with a halogenating agent in the presence of the fluorine-containing ether compound represented by the formula (1), halogen is added to the fluorine-containing olefin compound represented by the formula (2). As a result, a composition comprising the fluorine-containing ether compound represented by the formula (1) and a halogen adduct of the fluorine-containing olefin compound represented by the formula (2) is obtained. Further, in the step (A), when the fluorine-containing olefin compound represented by the formula (2) is reacted with an oxidant in the presence of the fluorine-containing ether compound represented by the formula (1), the fluorine-containing olefin compound represented by the formula (2) is converted to an oxide. As a result, a composition comprising the fluorine-containing ether compound represented by the formula (1) and an oxide of the fluorine-containing olefin compound represented by the formula (2) is obtained. In addition, in the step (A), when the fluorine-containing olefin compound represented by the formula (2) is reacted with a halogenating agent and an oxidant in the presence of the fluorine-containing ether compound represented by the formula (1), a composition comprising the fluorine-containing ether compound represented by the formula (1), a halogen adduct of the fluorine-containing olefin compound represented by the formula (2), and an oxide of the fluorine-containing olefin compound represented by the formula (2) is obtained.

In the step (A), when the fluorine-containing olefin compound represented by the formula (2) is reacted with a halogenating agent and/or oxidant to covert the fluorine-containing olefin compound represented by the formula (2) to a halogen adduct and/or oxide, the fluorine-containing ether compound represented by the formula (1) and hydrogen fluoride are preferably allowed to coexist. In the step (A), when the fluorine-containing ether compound represented by the formula (1) and hydrogen fluoride are allowed to coexist, the amount of hydrogen fluoride is preferably 0.1 mass % or less, more preferably 0.075 mass % or less, and even more preferably 0.05 mass % or less, based on the fluorine-containing ether compound represented by the formula (1). In the step (A), when the fluorine-containing ether compound represented by the formula (1) and hydrogen fluoride are allowed to coexist, the amount of hydrogen fluoride is preferably 0.0001 mass % or more, more preferably 0.0005 mass % or more, and even more preferably 0.001 mass % or more, based on the fluorine-containing ether compound represented by the formula (1).

Examples of halogen adducts include a chlorine adduct of the fluorine-containing olefin compound represented by the formula (2), a compound obtained by replacing hydrogen contained in the fluorine-containing olefin compound represented by the formula (2) with chlorine or bromine, a bromine adduct of the fluorine-containing olefin compound represented by the formula (2), and the like. Examples of oxides include a compound obtained by oxidizing the fluorine-containing olefin compound represented by the formula (2) to be converted to carboxylic acid, and the like.

The content of the fluorine-containing olefin compound represented by the formula (2) before the reaction of the step (A) is preferably 2 mass % or less based on the fluorine-containing ether compound represented by the formula (1).

The reaction of the step (A) is preferably a contact reaction between the fluorine-containing olefin compound represented by the formula (2) and a halogenating agent and/or oxidant.

The amount of halogenating agent supplied is preferably 1 mol or more, and preferably 2 mol or less, per mol of the fluorine-containing olefin compound represented by the formula (2). The amount of oxidant supplied is preferably 1 mol or more, and preferably 2 mol or less, per mol of the fluorine-containing olefin compound represented by the formula (2).

In the reaction of the step (A), an inert gas component, such as nitrogen gas, may be allowed to coexist, in terms of suppressing heat generation.

The reaction of the step (A) can be performed in a liquid phase or a gas phase. When the reaction is performed in a liquid phase, for example, a halogenating agent and/or oxidant are introduced into a crude liquid containing the fluorine-containing ether compound represented by the formula (1) and the fluorine-containing olefin compound represented by the formula (2) in a reactor, and the crude liquid is brought into contact with the halogenating agent and/or oxidant. When the reaction is performed in a gas phase, for example, a gasified crude liquid is brought into contact with a halogenating agent and/or oxidant in a reactor. In terms of increasing the recovery rate of the fluorine-containing ether compound represented by the formula (1), the reaction of the step (A) is preferably performed in a liquid phase.

When the reaction of the step (A) is performed in a liquid phase, it is preferable to bring the fluorine-containing olefin compound represented by the formula (2) into contact with a halogenating agent and/or oxidant by performing light irradiation in the presence of the fluorine-containing ether compound represented by the formula (1). As the light source for light irradiation, it is preferable to use a light source capable of irradiating ultraviolet rays having a wavelength of about 300 nm or more and 400 nm or less. Specific examples include arc lamps containing mercury, argon, or xenon; filament lamps containing tungsten and halogen, and the like. The halogenating agent and/or oxidant may be supplied continuously under light irradiation, or light irradiation may be started after introducing a predetermined amount thereof into the reactor all at once.

When the reaction of the step (A) is performed in a liquid phase, the reaction temperature is preferably 0° C. or more and preferably 30° C. or less, and more preferably less than 20° C. The reaction pressure is preferably 0.0 MPa or more and preferably 0.5 MPa or less, and more preferably atmospheric pressure. The reaction time is preferably 0.1 hours or more, and preferably 24 hours or less.

When the reaction of the step (A) is performed in a gas phase, it is preferably performed in the presence of a catalyst. Examples of catalysts include activated carbon, zeolite, alumina, silica-alumina, and the like.

When the reaction of the step (A) is performed in a gas phase, the reaction temperature is preferably 70° C. or more, and preferably 300° C. or less. The reaction pressure is preferably −0.05 MPa or more, and preferably 0.50 MPa or less. The reaction time is preferably 0.1 hours or more, and preferably 24 hours or less.

The reactor used in the liquid-phase reaction of the step (A) is, for example, a glass container, a glass-lined container, a resin-lined container, a SUS container, or the like.

The reactor used in the gas-phase reaction of the step (A) is, for example, a glass container, a glass-lined container, a resin-lined container, a SUS container, or the like.

Step (B)

Step (B) is a step of separating, from the composition comprising the fluorine-containing ether compound represented by the formula (1) and a halogen adduct of the fluorine-containing olefin compound represented by the formula (2) and/or an oxide of the fluorine-containing olefin compound represented by the formula (2) obtained in the step (A), the halogen adduct of the fluorine-containing olefin compound represented by the formula (2) and/or the oxide of the fluorine-containing olefin compound represented by the formula (2) to obtain a composition comprising the purified fluorine-containing ether compound represented by the formula (1).

In the composition obtained by the process of the step (B), the purity of the fluorine-containing ether compound represented by the formula (1) is generally more than 95 mass %, preferably 97 mass % or more, more preferably 99 mass % or more, even more preferably 99.3 mass % or more, and particularly preferably 99.5 mass % or more.

In the composition obtained by the process of the step (B), the purity of the fluorine-containing olefin compound represented by the formula (2) is generally 0.1 mass % or less, preferably 0.05 mass % or less, more preferably 0.01 mass % or less, even more preferably 0.005 mass % or less, and particularly preferably 0.001 mass % or less.

Distillation (particularly preferably rectification) is preferably used as the separation operation. For distillation (in particular, rectification), a distillation column (in particular, a rectification column) with multiple theoretical plates can be used, and either continuous distillation or batch distillation may be employed. The pressure at which distillation (in particular, rectification) is performed is preferably −0.05 MPa or more, and preferably 0.10 MPa or less. When distillation (in particular, rectification) is performed within such a pressure range, the boiling point difference between the fluorine-containing ether compound represented by the formula (1) and a halogen adduct of the fluorine-containing olefin compound represented by the formula (2) and/or an oxide of the fluorine-containing olefin compound represented by the formula (2) can be increased (e.g., a boiling point difference of 10° C. or more can be made). Accordingly, the separation operation and separation accuracy are improved.

The theoretical plate number of the distillation column (in particular, a rectification column) used in distillation (in particular, rectification) is preferably 2 or more, and preferably 30 or less. The reflux ratio of the distillation column (in particular, a rectification column) used in distillation (in particular, rectification) is preferably 2 or more, and preferably 50 or less. The distillation column (in particular, a rectification column) is preferably made of a material resistant to corrosive action, such as glass, stainless (SUS), Hastelloy, Inconel, or Monel; and more preferably made of SUS. Examples of fillers used in the distillation column (in particular, a rectification column) include Raschig rings, McMahon packing, and the like.

According to the production method of the present disclosure comprising the step (A) and the step (B) described above, a composition comprising a purified fluorine-containing ether compound represented by the formula (1): $CHX^1X^2CF_2OX^3$, wherein $X^1$ and $X^2$ are the same or different and each represents a hydrogen atom, a fluorine atom, or a trifluoromethyl group, and $X^3$ represents a $C_{1-r}$ alkyl group, provided that not both $X^1$ and $X^2$ are trifluoromethyl groups, can be obtained.

2. Composition

The composition of the present disclosure contains 1,1,2,3,3,3-hexafluoropropyl methyl ether (HFE-356mec) as an essential component, and further contains at least one of $CF_3CF{=}CFOCH_3$ and $CF_2{=}CFCF_2OCH_3$. In the present disclosure, the composition containing HFE-356mec and $CF_3CF{=}CFOCH_3$ and/or $CF{=}CFCF_2OCH_3$ can be used as a cleaner.

The composition of the present disclosure preferably contains HFE-356mec, $CF_3CF{=}CFOCH_3$, and $CF_2{=}CFCF_2OCH_3$. In this case, in terms of the stability of the composition, the stability of the material to be brought into contact with the composition, etc., the total content of $CF_3CF{=}CFOCH_3$ and $CF_2{=}CFCF_2OCH_3$ is preferably 0.1 mass % or less, more preferably 0.05 mass % or less, and even more preferably 0.01 mass % or less, based on HFE-356mec. Further, in terms of the stability of the composition, cost reduction during production of HFE-356mec, etc., the total content of $CF_3CF{=}CFOCH_3$ and $CF_2{=}CFCF_2OCH_3$ is preferably 0.00001 mass % or more, more preferably 0.00005 mass % or more, and even more preferably 0.0001 mass % or more, based on HFE-356mec.

The composition of the present disclosure may contain hydrogen fluoride. When the composition of the present disclosure contains hydrogen fluoride, the content of hydrogen fluoride is preferably 0.01 mass % or less, and more preferably 0.001 mass % or less, based on HFE-356mec.

The composition of the present disclosure may contain a small amount of water. The water content of the composition of the present disclosure is preferably 0.3 mass % or less, and more preferably 0.05 mass % or less, based on the total amount of HFE-356mec and $CF_3CF{=}CFOCH_3$ and/or $CF_2{=}CFCF_2OCH_3$. Because the composition of the present disclosure contains a small amount of water, the decomposition of the fluorine-containing olefin compound is suppressed, thereby improving the stability of the composition.

EXAMPLES

Embodiments of the present disclosure are described in more detail below while showing Examples. However, the present disclosure is not limited to these Examples. Hereinafter, the "room temperature" refers to 20 to 25° C.

Example 1-1: Contact Reaction in Liquid Phase Using Chlorine Gas 300 g of a crude product containing HFE-356mec with a purity of 94.4 mass %, a fluorine-containing olefin compound with a purity of 1.38 mass % ($CF_3CF{=}CFOCH_3$ with a purity of 1.28 mass % and $CF_2{=}CFCF_2OCH_3$ with a purity of 0.10 mass %), and hydrogen fluoride with a purity of 0.035 mass % was placed in a 1-L glass container. Then, while cooling the glass container to 0° C., chlorine gas was supplied at 20 ml/min for 30 minutes, and a contact reaction between the fluorine-containing olefin compound in the crude product and chlorine gas was performed in a liquid phase at a pressure of 0.0 MPa. Thereafter, 25 g of a 10 mass % sodium sulfite aqueous solution was added, followed by stirring for 30 minutes. After the elimination of chlorine gas was confirmed using potassium iodide starch paper, the organic phase was separated. The separated organic phase was washed with water to obtain 246 g of a composition containing HFE-356mec (purity: 95.5 mass %) (purity of HFE-356mec: 95.5 mass %, recovery rate of HFE-356mec: 82%).

Example 1-2: Rectification in Rectification Column

A device equipped with a 500-mL glass container, a glass rectification column (theoretical plate number: 5) using a SUS filler, a capacitor (temperature of cooling water in capacitor: 0° C. to 5° C.), and a fractionator was prepared, 220 g of the HFE-356mec-containing composition (246 g) obtained in Example 1-1 was added to the device, and the total reflux condition was maintained for 1 hour. After that, fractional distillation was started at a reflux ratio of 50, and rectification was completed when 177 g of a fraction was recovered. The GC analysis of the obtained fraction confirmed that the purity of HFE-356mec was 99.9 mass % (recovery rate: 80%) and the purity of the fluorine-containing olefin compound was 0.002 mass %. The purity of the hydrogen fluoride was 0.0002 mass %. The GC analysis of the obtained fraction could not confirm the presence of a chlorine adduct of the fluorine-containing olefin compound and an oxide of the fluorine-containing olefin compound.

Example 1-3: Contact Reaction in Liquid Phase Using Chlorine Gas 300 g of a crude product containing HFE-356mec with a purity of 93.0 mass %, a fluorine-containing olefin compound with a purity of 1.84 mass % ($CF_3CF{=}CFOCH_3$ with a purity of 1.74 mass % and $CF_2{=}CFCF_2OCH_3$ with a purity of 0.10 mass %), and hydrogen fluoride with a purity of 0.035 mass % was placed in a 1-L SUS container. Then, chlorine gas was supplied at 173 ml/min for 10 minutes under room temperature conditions, and a contact reaction between the fluorine-containing olefin compound in the crude product and chlorine gas was performed in a liquid phase at a pressure of 0.3 MPa. Thereafter, 25 g of a 10 mass % sodium sulfite aqueous solution was added, followed by stirring for 30 minutes. After the elimination of chlorine gas was confirmed using potassium iodide starch paper, the organic phase was separated. The separated organic phase was washed with water to obtain 285 g of a composition containing HFE-356mec (purity of HFE-356mec: 94.5 mass %, recovery rate of HFE-356mec: 96.5%).

Example 1-4: Contact Reaction in Gas Phase Using Chlorine Gas 300 g of a crude product containing HFE-356mec with a purity of 93.0 mass %, a fluorine-containing olefin compound with a purity of 1.84 mass % ($CF_3CF{=}CFOCH_3$ with a purity of 1.74 mass % and $CF_2{=}CFCF_2OCH_3$ with a purity of 0.10 mass %), and hydrogen fluoride with a purity of 0.035 mass % was placed in a 1-L SUS container. The reactor was heated to 70° C., chlorine gas was supplied at 173 ml/min for 10 minutes, and a contact reaction between the fluorine-containing olefin compound in the crude product and chlorine gas was performed in a gas phase at a pressure of 0.4 MPa. Thereafter, 25 g of a 10 mass % sodium sulfite aqueous solution was added, followed by stirring for 30 minutes. After the elimination of chlorine gas was confirmed using potassium iodide starch paper, the organic phase was separated. The separated organic phase was washed with water to obtain 282 g of a composition containing HFE-356mec (purity of HFE-356mec: 94.2 mass %, recovery rate of HFE-356mec: 95.2%).

Example 1-5: Rectification in Rectification Column

A device equipped with a 500-mL glass container, a glass rectification column (theoretical plate number: 5) using a SUS filler, a capacitor (temperature of cooling water in capacitor: 0° C. to 5° C.), and a fractionator was prepared, 220 g of the HFE-356mec-containing composition (261 g) obtained in Example 1-3 was added to the device, and the total reflux condition was maintained for 1 hour. After that, fractional distillation was started at a reflux ratio of 50, and rectification was completed when 99 g of a fraction was recovered. The GC analysis of the obtained fraction confirmed that the purity of HFE-356mec was 99.9 mass % (recovery rate: 45%) and the purity of the fluorine-containing olefin compound was 0.003 mass %. The purity of the hydrogen fluoride was 0.0002 mass %. The GC analysis of the obtained fraction could not confirm the presence of a chlorine adduct of the fluorine-containing olefin compound and an oxide of the fluorine-containing olefin compound.

Example 2-1: Contact Reaction in Liquid Phase Using Sodium Hypochlorite 220 g of a crude product containing HFE-356mec with a purity of 94.4 mass %, a fluorine-containing olefin compound with a purity of 1.37 mass % ($CF_3CF{=}CFOCH_3$ with a purity of 1.27 mass % and $CF_2{=}CFCF_2OCH$; with a purity of 0.10 mass %), and hydrogen fluoride with a purity of 0.035 mass %, and 66 g of a 12 mass % sodium hypochlorite aqueous solution were placed in a 1-L glass container. Then, stirring was performed at 54° C. under reflux for 1.5 hours, and a contact reaction between the fluorine-containing olefin compound in the crude product and sodium hypochlorite was performed in a liquid phase at a pressure of 0.0 MPa. 1.5 hours after stirring, the residual of the fluorine-containing olefin compound (purity: 0.474 mass %) was confirmed by GC. Then, an additional 33 g of 12 mass % sodium hypochlorite aqueous solution was added every hour for a total of three additions (99 g in total was added). However, the residual of the fluorine-containing olefin compound (purity: 0.07 mass %) was confirmed by GC; therefore, the resultant was returned to room temperature and stirred for 16 hours. Thereafter, 15.5 g of a 10 mass % sodium sulfite aqueous solution was added, followed by stirring for 30 minutes. After the elimination of sodium hypochlorite was confirmed using potassium iodide starch paper, the organic phase was separated. The separated organic phase was washed with water to obtain 186 g of a composition containing HFE-356mec (purity of HFE-356mec: 95.7 mass %, recovery rate of HFE-356mec: 85%).

Example 2-2: Contact Reaction in Liquid Phase Using Sodium Hypochlorite 220 g of a crude product containing HFE-356mec with a purity of 94.4 mass %, a fluorine-containing olefin compound with a purity of 1.37 mass % ($CF_3CF{=}CFOCH_3$ with a purity of 1.27 mass % and $CF_2{=}CFCF_2OCH_3$ with a purity of 0.10 mass %), and hydrogen fluoride with a purity of 0.035 mass %, and 66 g of a 12 mass % sodium hypochlorite aqueous solution were placed in a 1-L glass container. Then, the resultant was stirred at room temperature for 22 hours, and a contact reaction between the fluorine-containing olefin compound in the crude product and sodium hypochlorite was performed in a liquid phase at a pressure of 0.0 MPa. Thereafter, 15.5 g of a 10 mass % sodium sulfite aqueous solution was added, followed by stirring for 30 minutes. After the elimination of sodium hypochlorite was confirmed using potassium iodide starch paper, the organic phase was separated. The separated organic phase was washed with water to obtain 183 g of a composition containing HFE-356mec (yield of HFE-356mec: 83%).

Example 2-3: Rectification in Rectification Column

A device equipped with a 500-mL glass container, a rectification column (theoretical plate number: 5) using a SUS filler, a capacitor (temperature of cooling water in capacitor: 0° C. to 5° C.), and a fractionator was prepared, 90 g of the HFE-356mec-containing composition (183 g) obtained in Example 2-2 was added, and the total reflux condition was maintained for 1 hour. After that, fractional distillation was started at a reflux ratio of 50, and rectification was completed when 71 g of a fraction was recovered. The GC analysis of the obtained fraction confirmed that the purity of HFE-356mec was 99.9 mass % (recovery rate: 79%) and the purity of the fluorine-containing olefin compound was 0.003 mass %. The purity of the hydrogen fluoride was 0.0002 mass %. The GC analysis of the obtained fraction could not confirm the presence of a chlorine adduct of the fluorine-containing olefin compound and an oxide of the fluorine-containing olefin compound.

Example 2-4: Rectification in Rectification Column

A device equipped with a 500-mL glass container, a rectification column (theoretical plate number: 2) using a SUS filler, a capacitor (temperature of cooling water in capacitor: 0° C. to 5° C.), and a fractionator was prepared, 90 g of the HFE-356mec-containing composition (183 g) obtained in Example 2-2 was added, and the total reflux condition was maintained for 1 hour. After that, fractional distillation was started at a reflux ratio of 50, and rectification was completed when 69 g of a fraction was recovered. The GC analysis of the obtained fraction confirmed that the purity of HFE-356mec was 99.8 mass % (recovery rate: 76%) and the purity of the fluorine-containing olefin compound was 0.003 mass %. The purity of the hydrogen fluoride was 0.0002 mass %. The GC analysis of the obtained fraction could not confirm the presence of a chlorine adduct of the fluorine-containing olefin compound and an oxide of the fluorine-containing olefin compound.

Example 3-1: Contact Reaction in Liquid Phase Using Bromine 2918 g of a crude product containing HFE-356mec with a purity of 93 mass %, a fluorine-containing olefin compound with a purity of 1.38% ($CF_3CF{=}CFOCH_3$ with a purity of 1.28 mass % and $CF_2{=}CFCF_2OCH_3$ with a purity of 0.10 mass %), and hydrogen fluoride with a purity of 0.025 mass % was placed in a 5-L reactor. Then, the reactor was cooled in an ice bath to an internal temperature of 5° C. or less, and 133 g of bromine was added dropwise to the reactor. After completion of dropping, the inside of the reactor was returned to room temperature, stirring was performed at room temperature for 10 hours, and a contact reaction between the fluorine-containing olefin compound in the crude product and bromine was performed in a liquid phase. Then, the obtained reaction liquid was transferred to a 5-L plastic bucket, and 500 g of ice water and 50 g of sodium bicarbonate were added, followed by stirring. After confirming basicity with pH test paper, sodium thiosulfate (40 g) was added. After that, potassium iodide starch paper was used to confirm that excess bromine was removed. Next, the reaction liquid was transferred to a separating funnel, and the lower layer was taken out. As a result, the product was a colorless and transparent liquid. The product was analyzed by gas chromatography/mass spectrometry (GC/MS) and structurally analyzed by NMR spectrum. The results of mass spectrometry and structural analysis confirmed that the purity of HFE-356mec was 96.1 mass % and the recovery rate of HFE-356mec was 96% (yield: 2793 g).

Example 3-2: Rectification in Rectification Column

The product obtained in Example 3-1 was transferred to a 3-L round-bottomed flask equipped with a mantle heater and an internal thermometer in advance, and a glass Oldershaw rectification column (theoretical plate number: 20) equipped with a capacitor and a fractionator was attached to the top of the round-bottomed flask. The mantle heater was set at 100° C., and the total reflux condition was maintained for 1 hour. Thereafter, fractional distillation was started at a reflux ratio of 50, and purification was terminated when 2725 g of a fraction was recovered. The obtained fraction was analyzed by GC/MS and structurally analyzed by NMR spectrum. The results of mass spectrometry and structural analysis showed that the recovery rate of HFE-356mec was calculated from Example 3-1 to be 93%, and the purity of HFE-356mec was 99.95 mass %. The purity of the fluorine-containing olefin compound was 0.003 mass %. The GC analysis of the obtained fraction could not confirm the presence of a bromine adduct of the fluorine-containing olefin compound and an oxide of the fluorine-containing olefin compound.

Example 4

A solvent containing HFE-356mec, $CF_3CF{=}CFOCH_3$, and hydrogen fluoride (content of $CF_3CF{=}CFOCH_3$: 0.004 mass % based on HFE-356mec, content of hydrogen fluoride: 0.0002 mass % based on HFE-356mec) was placed in a glass flask equipped with a Dimroth condenser. Further, test pieces of iron, copper, zinc, and aluminum were each placed in the flask and refluxed by heating to 53° C. in air under atmospheric pressure, and the stability of the solvent and each test piece was observed. After 72 hours, no acid was generated in the solvent, and no change such as corrosion was observed in any of the test pieces.

Example 5

The observation was made under the same conditions as in Example 4, except that the content of $CF_3CF{=}CFOCH_3$ was changed to 0.004 mass % based on HFE-356mec, and 0.3 mass % of water was added to the solvent. After 72 hours, no acid was generated in the solvent, and no change such as corrosion was observed in any of the test pieces.

Example 6

The observation was made under the same conditions as in Example 4, except that the content of $CF_3CF{=}CFOCH_3$ was changed to 0.009 mass % based on HFE-356mec, the content of hydrogen fluoride was changed to 0.0004 mass % based on HFE-356mec, and 0.03 mass % of water was added to the solvent. After 72 hours, no acid was generated in the solvent, and no change such as corrosion was observed in any of the test pieces.

Comparative Example 1

A solvent containing HFE-356mec, $CF_3CF{=}CFOCH_3$, $CF_2CF{=}CF_2OCH_3$, and hydrogen fluoride (content of $CF_3CF{=}CFOCH_3$: 1.38 mass % based on HFE-356mec, content of $CF_2CF{=}CF_2OCH_3$: 0.8 mass % based on HFE-356mec, content of hydrogen fluoride: 0.0004 mass % based on HFE-356mec) was placed in a glass flask equipped with a Dimroth condenser, and 0.3 mass % of water was added to the solvent. Further, test pieces of iron, copper, zinc, and aluminum were each placed in the flask and refluxed by heating to 53° C. in air under atmospheric pressure, and the stability of the solvent and each test piece was observed. After 72 hours, acid was generated in the solvent, and corrosion was observed in all of the test pieces.

The present disclosure provides the invention according to the following embodiments.

Item 1.

A method for producing a composition comprising a purified fluorine-containing ether compound, the method comprising:

(A) reacting, in the presence of a fluorine-containing ether compound represented by formula (1): $CHX^1X^2CF_2OX^3$, wherein $X^1$ and $X^2$ are the same or different and each represents a hydrogen atom, a fluorine atom, or a trifluoromethyl group, and $X^3$ represents a $C_{1-6}$ alkyl group, provided that not both $X^1$ and $X^2$ are trifluoromethyl groups, a fluorine-containing olefin compound represented by formula (2): $CX^1X^2{=}CF(CF_2)_nOX^3$, wherein n represents 0 or 1, and $X^1$, $X^2$, and $X^3$ are as defined above, provided that when $X^1$ or $X^2$ is a trifluoromethyl group, n is 0, and not both $X^1$ and $X^2$ are trifluoromethyl groups, with a halogenating agent and/or oxidant to convert the fluorine-containing olefin compound represented by the formula (2) to a halogen adduct and/or oxide, thereby obtaining a composition comprising the fluorine-containing ether compound represented by the formula (1) and the halogen adduct and/or oxide; and (B) separating the halogen adduct and/or oxide from the composition obtained in the step (A) to obtain a composition comprising a purified fluorine-containing ether compound.

Item 2.

The production method according to Item 1, wherein the halogenating agent is a chlorinating agent and/or brominating agent.

Item 3.

The production method according to Item 1 or 2, wherein in the step (A), the reaction is performed in a liquid phase.

Item 4.

The production method according to any one of Items 1 to 3, wherein in the step (B), the composition obtained in the step (A) is rectified in a rectification column to separate the halogen adduct and/or oxide from the composition obtained in the step (A).

Item 5.

The production method according to any one of Items 1 to 4, wherein the fluorine-containing ether compound represented by the formula (1) is 1,1,2,3,3,3-hexafluoropropyl methyl ether (HFE-356mec).

Item 6.

The production method according to any one of Items 1 to 5, wherein the fluorine-containing olefin compound represented by the formula (2) is $CF_3CF{=}CFOCH_3$ and/or $CF_2{=}CFCF_2OCH_3$.

Item 7.

A composition comprising 1,1,2,3,3,3-hexafluoropropyl methyl ether (HFE-356mec), and $CF_3CF{=}CFOCH_3$ and/or $CF_2{=}CFCF_2OCH_3$.

Item 8.

The composition according to Item 7, wherein the total content of $CF_3CF{=}CFOCH_3$ and $CF_2{=}CFCF_2OCH_3$ is 0.1 mass % or less based on HFE-356mec.

Item 9.

The composition according to Item 7 or 8, wherein the composition further comprises hydrogen fluoride, and wherein the content of the hydrogen fluoride is 0.01 mass % or less based on HFE-356mec.

The invention claimed is:

1. A composition comprising 1,1,2,3,3,3-hexafluoropropyl methyl ether (HFE-356mec), $CF_3CF{=}CFOCH_3$ and/or $CF_2{=}CFCF_2OCH_3$, and hydrogen fluoride, wherein the total content of $CF_3CF{=}CFOCH_3$ and $CF_2{=}CFCF_2OCH_3$ is 0.00001 mass % or more and 0.1 mass % or less based on HFE-356mec, wherein the hydrogen fluoride is present in the composition, and wherein the content of the hydrogen fluoride is 0.01 mass % or less based on HFE-356mec.

2. The composition according to claim 1, wherein the purity of HFE-356mec is more than 95 mass % in the composition.

3. The composition according to claim 1, wherein the composition further comprises water, wherein the water is present in the composition, and wherein the content of the water is 0.3 mass % or less, based on the total amount of HFE-356mec and $CF_3CF{=}CFOCH_3$ and/or $CF_2{=}CFCF_2OCH_3$.

4. The composition according to claim 2, wherein the composition further comprises water, wherein the water is present in the composition, and wherein the content of the water is 0.3 mass % or less, based on the total amount of HFE-356mec and $CF_3CF{=}CFOCH_3$ and/or $CF_2{=}CFCF_2OCH_3$.

* * * * *